Figure 2:
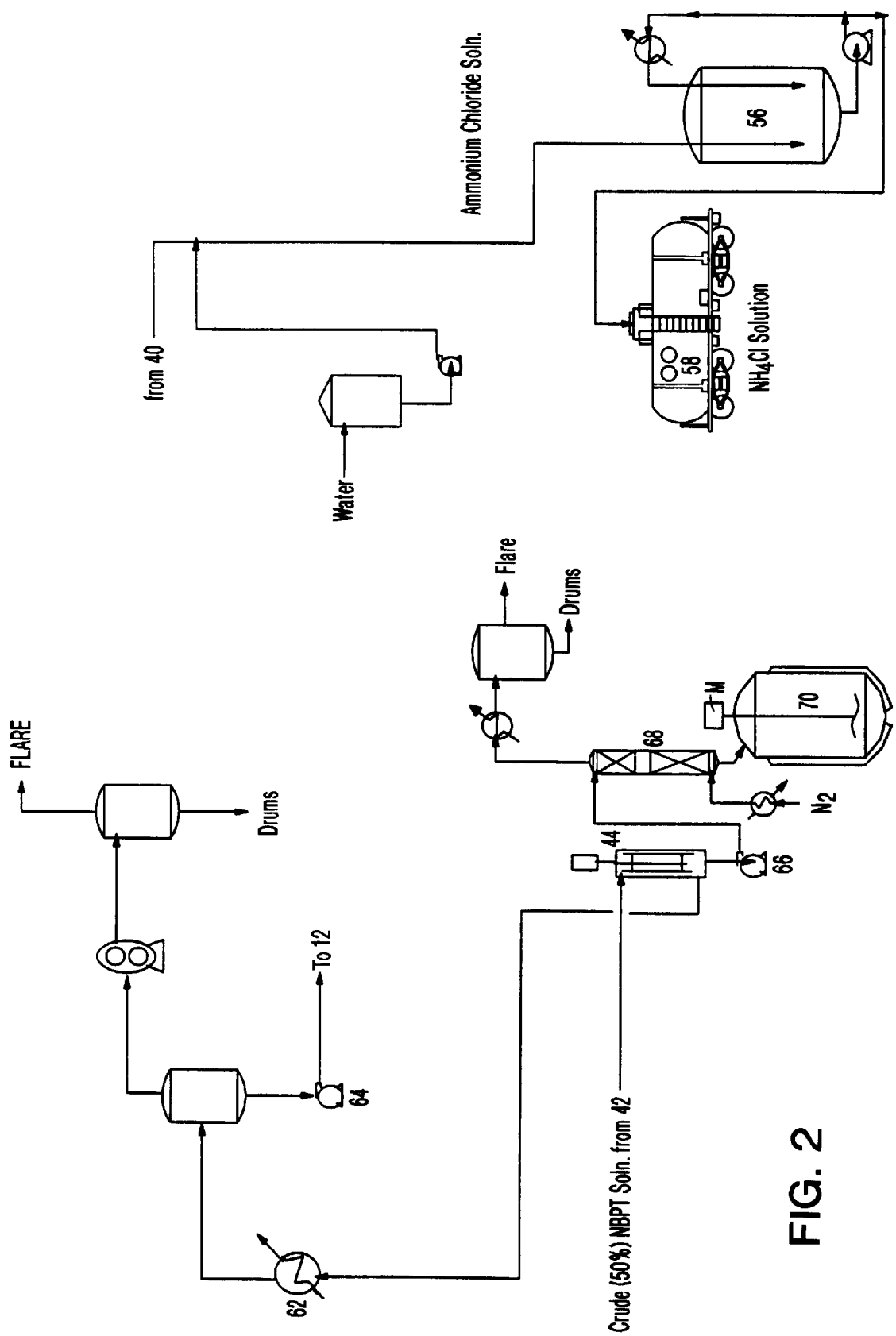

United States Patent [19]
Cheng et al.

[11] Patent Number: 5,955,630
[45] Date of Patent: *Sep. 21, 1999

[54] RECOVERY OF N-HYDROCARBYLTHIOPHOSPHORIC TRIAMIDES AND N-HYDROCARBYLPHOSPHORIC TRIAMIDES FROM REACTION MIXTURES

[75] Inventors: Chi Hung Cheng; Gerald M. Sulzer, both of Baton Rouge, La.

[73] Assignee: Albemarle Corporation, Richmond, Va.

[ * ] Notice: This patent is subject to a terminal disclaimer.

[21] Appl. No.: 08/786,535

[22] Filed: Jan. 21, 1997

[51] Int. Cl.[6] ....................................................... C07F 9/22
[52] U.S. Cl. ............................................................. 564/14
[58] Field of Search ................................................ 564/14

[56] References Cited

U.S. PATENT DOCUMENTS

| | | | |
|---|---|---|---|
| 4,242,325 | 12/1980 | Bayless et al. | 424/210 |
| 4,530,714 | 7/1985 | Kolc et al. | 71/28 |
| 5,079,380 | 1/1992 | Thunberg | 558/346 |

FOREIGN PATENT DOCUMENTS

| | | |
|---|---|---|
| 830800 | 3/1960 | United Kingdom . |
| 848952 | 9/1960 | United Kingdom . |

OTHER PUBLICATIONS

L. A. Cates; "Phosphorus–Nitrogen Compounds. XI. Phosphamidase Studies. I. Unsubstituted Amides[1,2]"; J. Med Chem., vol. 13, 1970; pp. 301–302.

M. Goehring, et al.; "Uber Phosphor–Stickstoffverbindungen, I. Mitteil.: Zur Kenntnis der Amide der Phosphorsaure und der Thiophosphorsaure"; Chem. Ber., No. 7, 1956; pp. 1768–1774.

Kendall, et al; "Addition Compounds of Ammonia With The Ammonium Halides"; J. Amer. Chem. Soc., 1920, vol. 42; pp. 1141–1145.

Yamamoto, et al., "Measurement of Heat of Mixing for Ammonium Chloride + Ammonia System at 25° C"; The Canadian Journal of Chemical Engineering, vol. 66, 1988; pp. 127–130.

Abe, et al., "Regarding The Solubility of Di– And Trichlorides In Liquid Ammonia (Part 3) Solubility Of Ammonium Chloride And Vapor Pressure Of Its Solution"; 1935; J. Soc. Chem. Ind. Japan, vol. 38, pp. 1402–1406.

*Primary Examiner*—Peter O'Sullivan
*Attorney, Agent, or Firm*—Philip M Pippenger

[57] ABSTRACT

N-hydrocarbylthiophosphoric triamide is separated or recovered from a liquid mixture comprising N-hydrocarbylthiophosphoric triamide, inert organic solvent, and optionally but preferably, tertiary amine, by continuously introducing a stream of the liquid mixture into a wiped film evaporator operating at a temperature in the range of about 60 to about 140° C., and at a pressure that avoids solids formation on the heating surface of the wiped film evaporator, and continuously collecting the resultant N-hydrocarbylthiophosphoric triamide product.

44 Claims, 2 Drawing Sheets

FIG. 1

RECOVERY OF N-HYDROCARBYLTHIOPHOSPHORIC TRIAMIDES AND N-HYDROCARBYLPHOSPHORIC TRIAMIDES FROM REACTION MIXTURES

BACKGROUND

N-hydrocarbylthiophosphoric triamides and N-hydrocarbylphosphoric triamides are known to be effective urease inhibitors for use with urea-based fertilizer compositions. Note, for example, U.S. Pat. No. 4,530,714 to J. F. Kole, et al.

Known procedures for preparing N-hydrocarbylthiophosphoric triamides and N-hydrocarbylphosphoric triamides involve batch operations in which an N-hydrocarbylaminothiophosphoryl dichloride or N-hydrocarbylaminophosphoryl dichloride is formed in a first reaction, recovered, and often purified. In a second reaction, the N-hydrocarbylaminothiophosphoryl dichloride or N-hydrocarbylaminophosphoryl dichloride is reacted with ammonia to produce a slurry from which co-product ammonium chloride is separated by filtration. See for example, U.S. Pat. No. 4,530,714.

In commonly-owned copending U.S. application Ser. No. 08/786,396, filed Jan. 21, 1997, an excellent continuous process for the production of N-hydrocarbylthiophosphoric triamides is described. In one of its preferred embodiments, the process results in the formation of a concentrated solution of N-hydrocarbylthiophosphoric triamide in a mixture of a solvent (most preferably tetrahydrofuran) and a tertiary amine (most preferably triethylamine).

Unfortunately, N-hydrocarbylthiophosphoric triamides such as N-alkylthiophosphoric triamides, and N-hydrocarbylphosphoric triamides such as N-alkylphosphoric triamides are relatively unstable when subjected to elevated temperatures. Consequently, when recovering N-hydrocarbylthiophosphoric triamides from solutions in organic media such as ethers and/or tertiary amines, etc., using various conventional distillation procedures, the triamide tends to undergo an undesirable amount of thermal degradation. Not only is this wasteful of desired product, but the formation of thermally degraded species in the product reduces its purity and sales appeal. Alternative methods of recovering these triamides from solution such as crystallization and freeze drying can overcome the thermal decomposition problem but they are expensive to perform and involve troublesome solids processing. An efficient, cheaper method of overcoming these problems is desired.

THE INVENTION

This invention has successfully overcome the foregoing problems associated with the recovery of N-hydrocarbylthiophosphoric triamides and N-hydrocarbylphosphoric triamides from solutions in organic media, while at the same time providing a separation process which not only is ideally-suited for large scale commercial operation but which, in addition, actually improves the efficiency of the product recovery step itself, is low in cost, and avoids solids handling.

In accordance with this invention there is provided a process for separating or recovering N-hydrocarbylthiophosphoric triamide or N-hydrocarbylphosphoric triamide from a liquid mixture comprising N-hydrocarbylthiophosphoric triamide (HTPT) or N-hydrocarbylphosphoric triamide (HPT) and at least one inert organic solvent. Preferably, the organic solvent is sufficiently inert such that it can also be used in the synthesis of the HTPT or HPT and avoid the need to exchange the reaction solvent(s) prior to the HTPT or HPT recovery. While any solvent meeting these criteria can be used, it is preferred to use a solvent that boils at one or more temperatures in the range of about 40 to about 120° C. and preferably in the range of about 55 to about 90° C. at ordinary atmospheric pressures. Thus use can be made of liquid paraffinic, cycloparaffinic, and/or aromatic hydrocarbons, liquid halocarbons and halohydrocarbons, ethers, esters, and other organic liquids which do not interfere with the desired reactions. Ethers, especially cyclic ethers such as 1,4-dioxane (bp 101° C.), 1,3-dioxolane (bp 78° C.), tetrahydrofuran (bp 66° C.), methyltetrahydrofuran (bp 80° C.), and tetrahydropyran (bp 88° C.), are preferred. Of the various suitable solvents, tetrahydrofuran is particularly preferred because of its good solvency properties, desirable boiling point, ready availability, and relatively low cost. The liquid mixture may also be comprised of a tertiary amine which typically is used as an acid acceptor in the first stage reaction in two-stage synthesis of the HTPT or HPT, and is carried over into the second stage reaction. Preferably, the tertiary amine boils at one or more temperatures in the range of about 40 to about 130° C. and preferably in the range of about 50 to about 100° C. at ordinary atmospheric pressures. Suitable amines include heterocylic tertiary amines, such as pyridine (bp 115–6° C.) and 2-picoline (bp 128° C.), or trialkyl amines, such as N,N-diethylmethylamine (bp 63–5° C.) and triethylamine (bp 89.4° C.). Of the various suitable tertiary amines, triethylamine is particularly preferred because of it's desirable boiling point, ready availability and relatively low cost.

The separation or recovery process comprises continuously introducing a stream of such liquid mixture into a wiped film evaporator operating at a temperature in the range of about 60 to about 140° C., and at a sub-atmospheric pressure that avoids solids formation on the heating surface of the wiped film evaporator, and continuously collecting (e.g., by withdrawing therefrom) N-hydrocarbylthiophosphoric triamide or N-hydrocarbylphosphoric triamide so formed. The minimum operating pressure needed to avoid this solids formation will depend on the selection of solvents comprising the HTPT or HPT solution. For the solvents indicated above, the minimum operating pressure to avoid solids formation is expected to fall in the range of about 50–150 torr absolute. Where the triamide is N-n-butylthiophosphoric triamide (BTPT) and the liquid mixture is a solution of BTPT, tetrahydrofuran, and triethylamine, the wiped film evaporator is operated at a pressure higher than about 90 torr absolute to avoid solids formation. Use of solvents having boiling points higher than the tetrahydrofuran/triethylamine mixture would be expected to have a lower minimum allowable operating pressure, and vice versa. The actual minimum allowable operating pressure should be determined experimentally for the specific solvent/triamide solution to be utilized in the process. The average residence time of the triamide in the wiped-film evaporator is preferably kept substantially constant throughout the operation, and is kept below about one (1) minute.

Without being bound by theoretical considerations, it is believed that when processing solutions of N-hydrocarbylthiophosphoric triamide (HTPT) or N-hydrocarbylphosphoric triamide (HPT) not in accordance with this invention, harmful formation of solids on the heating surface of the wiped film evaporator occurs in the following manner: As the solution passes along the heating surface of the wiped film evaporator, the solvent(s) evaporate whereby the normal increase in the temperature of the solution due to conduction of heat from the surface is at least partially offset by the cooling effect of the vaporization of the solvent(s). At the same time, the concentration of the HTPT or HPT in the flowing solution continues to slowly increase because of gradual continuous removal of the solvent(s). When the temperature of the solution drops below the freezing point of the evaporating materials, solids are formed. These solids, which remain relatively enriched in solvents, bypass the heating surface of the wiped film evaporator, and drop directly into the product receiver, resulting in unsteady operation and product having an undesirably high content of residual solvents. However, when conducting the process of this invention, the adverse effects of solids formation are markedly suppressed, the operation of the wiped film evaporator is stable, and the resultant HTPT or HPT product is of high purity. In fact, when in conducting the process pursuant to this invention using the particularly preferred solvents [i.e., a mixture of tetrahydrofuran (THF) and triethylamine (TEA)], the conditions used typically result in separation and recovery of a triamide such as N-n-butylthiophosphoric triamide which contains no more than a total of about 1.7 wt. % tetrahydrofuran and triethylamine.

The N-hydrocarbylthiophosphoric triamides and N-hydrocarbylphosphoric triamides utilized in the process of this invention are those which exist as solids at room temperature with melting points in the range of 50–130° C. and which are soluble to the extent of at least 0.4 grams per milliliter at 20° C. in a solvent comprising 80 to 100 wt. % of one or more inert organic solvents of any of the types referred to above, with the balance, if any, being tertiary amine. Generally speaking, such triamides include, for example, those in which the hydrocarbyl group contains up to about 8 carbon atoms. The preferred triamide is N-n-butylthiophosphoric triamide. The preferred solvent mixture is comprised of THF and triethylamine (TEA).

The hydrocarbyl group of the triamide can be any hydrocarbyl group such as an alkyl, cycloalkyl, alkenyl, cycloalkenyl, alkynyl, aryl, aralkyl, or cycloalkylalkyl group. Of such compounds N-alkylthiophosphoric triamides, N-cycloalkylthiophosphoric triamides, and N-arylthiophosphoric triamides are preferred, and of these, N-alkylthiophosphoric triamides having 2 to 6 carbon atoms in the molecule are especially preferred. Most preferred is N-n-butylthiophosphoric triamide.

The mixtures treated pursuant to this invention will typically be mixtures containing about 5 to about 60 wt. % of N-hydrocarbylthiophosphoric triamide or N-hydrocarbylphosphoric triamide, about 40 to about 95 wt. % of inert organic solvent, about 0 to about 20 wt. % of tertiary amine, and optionally, up to about 12 wt. % of phosphorus-containing impurities. Phosphorus impurities which can be present include such materials as thiophosphoric triamide, N,N'-dihydrocarbylthiophosphoric triamide, N,N',N"-trihydrocarbylthiophosphoric triamide, linear or cyclic oligomers of the hydrocarbylthiophosphoric triamide, phosphoric triamide, N,N'-dihydrocarbylphosphoric triamide, N,N',N"-trihydrocarbylphosphoric triamide, and linear or cyclic oligomers of the hydrocarbylphosphoric triamide.

Preferably, the wiped film evaporator is operated at a temperature in the range of about 60 to about 130° C. Temperatures as high as 130 or even 140° C. can be effectively used because of the short residence time of the solution within the evaporator. It is particularly preferred to operate the wiped film evaporator at a temperature in the range of about 90 to about 130° C.

Among the advantages of this invention are that the use of a wiped film evaporator under the above operating conditions eliminates the need for low temperature refrigeration (<10° C.) to condense the solvent. In addition, the low residence time in the wiped film evaporator allows use of temperatures that are high enough to achieve essentially complete solvent removal without significant thermal degradation of product which would result if using a more traditional flash unit.

Methods for the design and construction of wiped film evaporators are well known to those skilled in the art of wiped film manufacture. See, for example, *Chem. Eng.*, 1965, 72, 175–190 and *Chemical Engineering Progress*, December 1989, 12–15. There are also vendors, such as Pope Scientific and Pfaudler, who manufacture wiped film evaporators and who can supply assistance in obtaining a satisfactory design of apparatus for the particular operations to be conducted therewith. Included among the features of this invention are the utilization of a wiped film evaporator for effecting the separation and recovery of HTPT or HPT from solutions, preferably THF-TEA solutions, and the use with the wiped film evaporator of the foregoing operating conditions that enable the achievement of steady state operation with such solutions and the recovery of high purity N-hydrocarbylthiophosphoric triamide or N-hydrocarbylphosphoric triamide.

This invention is applicable to the separation and recovery of N-hydrocarbylthiophosphoric triamides and N-hydrocarbylphosphoric triamides from solutions, preferably THF-TEA solutions, formed in any manner, and thus in its broader aspects is essentially independent of the manner in which such solutions are formed. The only requirement is that the solution must be free from quantities of any substance that would prevent, or materially interfere with, the operation of the wiped film evaporator. In other words, the initial solution comprising HTPT, inert solvent, and tertiary amine and subjected to the process should be selected with the application of common sense and the ordinary skill of a chemist or chemical engineer.

In one embodiment the N-hydrocarbylthiophosphoric triamide or the N-hydrocarbylphosphoric triamide is formed by mixing and reacting ammonia and N-hydrocarbylaminothiophosphoryl dichloride or N-hydrocarbylaminophosphoryl dichloride in an inert organic solvent, in proportions (1) that are at least about 16 moles (and preferably at least about 20 moles) of ammonia per mole of N-hydrocarbylaminothiophosphoryl dichloride or N-hydrocarbylaminophosphoryl dichloride, (2) that produce a reaction mixture containing N-hydrocarbylthiophosphoric triamide or N-hydrocarbylthiophosphoric triamide, and (3) that keep in solution substantially all of the ammonium chloride co-product formed in the reaction, and maintaining the temperature of the reaction mixture high enough to keep ammonium chloride-ammonia complex from forming an appreciable amount of solid phase in said reaction mixture, but low enough to avoid significant reduction in yield of N-hydrocarbylthiophosphoric triamide or N-hydrocarbylphosphoric triamide. The reaction is an exothermic reaction and thus to control the temperature, the feed materials may be pre-cooled and/or heat can be removed from the reaction mixture at a suitable rate, for example by use of heat exchangers, internal cooling coils, or the like.

The following examples are given for the purposes of illustration, and are not intended to constitute limitations on the scope or practice of this invention. Unless otherwise specified all quantities and percentages in the Examples are by weight.

EXAMPLE 1

A solution composed of 53 wt. % of N-n-butylthiophosphoric triamide (BTPT) product of 95 wt. % purity, 43.5 wt. % of tetrahydrofuran (THF) and 3.5 wt. % triethylamine (TEA) was fed continuously into a two-inch glass, wiped film still (procured from Pope Scientific, Inc.) equipped with an external cold trap condenser containing dry ice/acetone, a heating jacket, a 1-liter distillate receiver flask, and four sample collectors for the recovered BTPT product. The vacuum system consisted of a high vacuum mechanical pump, a digital vacuum transmitter and readout, a dry ice trap, and a vacuum control system. The product temperature was varied by adjusting the heating oil temperature to the heating jacket. The vacuum was maintained by bleeding in nitrogen upstream of the vacuum pump.

It was observed that when the pressure was below 90 mm Hg absolute, solid was formed on the heating surface of the apparatus. Some of the solids dropped straight to the product receiver. When this occurred, the temperature and pressure would fluctuate erratically, resulting in unsteady operation.

In addition, as shown in Table 1, product decomposition becomes very severe when the temperature was raised from 130 to 149° C.

TABLE 1

| Run | Temp., ° C. | Pressure, Torr | % Decomposition | THF/TEA, wt %/wt % |
|---|---|---|---|---|
| 1 | 90 | 90 | nil | 1.5/0.2 |
| 2 | 109 | 90 | nil | 1.3/0.1 |
| 3 | 130 | 90 | 1 | 0.7/0.1 |
| 4 | 149 | 90 | 25 | 0.8/0.1 |

The above high temperature operations (e.g., Runs 1–3) are not feasible if using a traditional flash unit with minimal residence time (5–10 minutes), as degradation of the product was found to be excessive at temperatures of 100 and 110° C. Presented in Table 2 are the results of thermal stability tests conducted with BTPT at 100° C. and 110° C.

TABLE 2

| Temperature, ° C. | Time of Exposure, Min. | % Decomposition |
|---|---|---|
| 100 | 30 | 4.4 |
| 100 | 60 | 8.5 |
| 100 | 90 | 15.1 |
| 100 | 120 | 20.8 |
| 110 | 30 | 13.2 |
| 110 | 60 | 26.1 |
| 110 | 90 | 43.6 |
| 110 | 120 | 59.9 |

From the data in Table 2, it would be expected that about 2% product decomposition would occur even with only 5 minutes residence time in a traditional flash drum operating at 110° C.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

ADDENDUM

In the exercise of a superabundance of caution, for purposes of satisfying best mode requirements as interpreted from time to time by the courts, the following addendum is provided dealing with the continuous process of commonly-owned copending U.S. application Serial No. 08/786,396, filed Jan. 21, 1997, in which the separation and recovery process of this invention can be, and preferably is, employed.

Reactants

The principal reactants in the process are primary hydrocarbyl monoamine, thiophosphoryl chloride ($PSCl_3$), and ammonia. The hydrocarbyl group of the primary amine reactant can be any hydrocarbyl group such as alkyl, cycloalkyl, alkenyl, cycloalkenyl, alkynyl, aryl, aralkyl, or cycloalkylalkyl group. Typically the hydrocarbyl group will contain up to about 20 carbon atoms, and preferably up to about 10 carbon atoms. Of such compounds monoalkyl amines, monocycloalkylamines and monoarylamines are preferred, and of these, monoalkyl amines having 2 to 6 carbon atoms in the molecule are especially preferred. Most preferred as the amine reactant is n-butylamine.

The ammonia is preferably stored and handled in its liquid form. However, gaseous ammonia, or mixtures of gaseous and liquid ammonia, can also be used, if desired.

Solvent

At least one liquid inert organic solvent is employed in the process. While any solvent meeting these criteria can be used, it is preferred to use a solvent that boils at one or more temperatures in the range of about 40 to about 120° C. and preferably in the range of about 55 to about 90° C. at ordinary atmospheric pressures. Thus use can be made of liquid paraffinic, cycloparaffinic, and/or aromatic hydrocarbons, liquid halocarbons and halohydrocarbons, ethers, esters, and other organic liquids which do not interfere with the desired reactions. Ethers, especially cyclic ethers such as 1,4-dioxane, 1,3-dioxolane, tetrahydrofuran, methyltetrahydrofuran, and tetrahydropyran, are preferred. Preferably the solvent is recovered, most preferably by one or more flash distillations, and is used as recycle in the process.

Of the various suitable solvents, tetrahydrofuran is particularly preferred because of its good solvency properties, desirable boiling point, ready availability and low cost. In a well-designed facility, about 99% of the tetrahydrofuran can be recovered, and preferably the recovered tetrahydrofuran is used as recycle in the process.

HCl Acceptor

A tertiary amine is used as an acid acceptor for the by-product HCl formed in the first reaction. It is not consumed by the process, and in the preferred embodiments the tertiary amine is recycled in the process. Suitable tertiary amines include heterocyclic tertiary amines such as 3-picoline (bp ca. 143–144° C.), 4-picoline (bp ca. 143° C.), 4-chloropyridine (bp ca. 147–148° C.), 3-ethylpyridine (bp ca. 165–166° C.), and 4-ethylpyridine (bp ca. 166° C.), and trialkylamines such as tripropylamine (bp ca. 155–158° C.), and tri-sec-butylamine (bp ca. 191–192° C.). Relatively low boiling tertiary amines such as pyridine (bp ca. 115° C.), 2-picoline (bp ca. 128° C.), N,N-diethylmethylamine (bp 63–65° C.), and triethylamine (bp ca. 89° C.) are preferred.

From a cost-effectiveness standpoint, triethylamine is a particularly preferred tertiary amine. In a well-designed facility for the continuous process, about 99% of the triethylamine can be recovered, and preferably the recovered triethylamine is used as recycle in the process. Thus the process is capable of producing suitably high purity product (s) while at the same time being both highly efficient and environmentally friendly.

Reaction Conditions

The first stage reaction involving reaction between thiophosphoryl chloride and the primary amine is typically conducted at one or more temperatures in the range of about −20 to about 50° C., and preferably at one or more temperatures in the range of about 0 to about 15° C. The pressure conditions for this reaction are not important unless evaporative cooling is used to control reactor temperature. If using evaporative cooling, the reactor pressure is controlled such that the reaction mass will boil at the desired reactor temperature. Proportions of reactants in the first stage are essentially equimolar, and the mole ratio of primary amine to thiophosphoryl chloride is typically in the range of about 0.95 to about 1.1 moles of amine per mole of the $PSCl_3$. For best results, the mole ratio of primary amine to thiophosphoryl chloride is in the range of about 1.00 to about 1.05 moles of amine per mole of the $PSCl_3$.

The desired product of the first stage reaction is an N-hydrocarbylaminophosphoryl dichloride. Such compounds have the formula, $(H)(R)N—P(=S)Cl_2$, where R is a hydrocarbyl group.

As noted above, primary hydrocarbyl monoamine and tertiary amine are charged to the first reaction chamber as a preformed mixture which also includes one or more solvents, and the proportions of primary hydrocarbyl monoamine and tertiary amine in such preformed mixture are typically in a molar ratio range of about 1:1 to about 1:1.5 respectively. Typically, the proportions of such preformed mixture and the thiophosphoryl chloride fed to the first reaction chamber are such that per mole of thiophosphoryl chloride there are in the range of about 0.95 to about 1.1 moles of primary hydrocarbyl monoamine and in the range of about 0.95 to about 1.5 moles of tertiary amine.

In the second stage reaction between the N-hydrocarbylaminothiophosphoryl dichloride and ammonia, one or more temperatures in the range of about 5 to about 50° C. and one or more pressures in the range of about 15 to about 100 psig are typically employed, with the proviso that in any given situation, the temperature is high enough to keep the co-product ammonium chloride-ammonia complex in solution, yet low enough to avoid significant reduction in yield (e.g., a loss of more than 5 wt. % yield) of N-hydrocarbylthiophosphoric triamide. The N-hydrocarbylthiophosphoric triamides have the formula, $(H)(R)N—P(=S)(NH_2)_2$, where R is a hydrocarbyl group. Preferred conditions for the second stage reaction, especially when producing N-n-butylthiophosphoric triamide involve one or more temperatures in the range of about 8 to about 15° C. and one or more pressures in the range of about 25 to about 40 psig. In the second stage reaction the proportions of ammonia to the N-hydrocarbylaminothiophosphoryl dichloride are such that there are at least about 16 moles of ammonia, and preferably at least about 20 moles of ammonia, per mole of N-hydrocarbylaminothiophosphoryl dichloride. In theory there is no upper limit on the amount of ammonia used as the excess ammonia does not materially interfere with the desired reactions. Thus the amount of excess ammonia above the foregoing minimum amounts is largely a matter of common sense and practicality; i.e., the larger the excess, the larger the amounts of ammonia that need to be recovered and recycled.

The amount of solvent used in the process is an amount sufficient to provide a suitably fluid reaction medium, and thus is largely a matter of choice, common sense, and practicality. Thus unduly excessive amounts of solvent should be avoided as the larger the amount used, the larger the amount that needs to be recovered and recycled.

The first stage and the second stage reactions are both exothermic reactions and thus suitable equipment should be provided to ensure that adequate cooling capacity is available for each of the two stages. In a preferred embodiment, the heat of reaction from the first stage reaction mixture is removed by continuously circulating a portion of that reaction mixture from the first stage reaction chamber into a heat exchanger where heat is removed by a cooling medium, and thence back to the first reaction chamber. In a particularly preferred embodiment the heat of reaction from the first stage reaction mixture is removed by controlling the pressure such that the reaction mixture boils and the vapors from the boiling mixture are condensed in a dephlegmator heat exchanger and refluxed back to the first reaction chamber.

In another preferred embodiment the reaction mixture in the first reaction chamber is continuously stirred or agitated by a mechanical stirrer or agitator, and the preformed mixture and the thiophosphoryl chloride are both fed into such reaction mixture below the surface thereof and in close proximity to the stirrer/agitator to ensure prompt and rapid mixing of these feeds.

In still another preferred embodiment, the heat of reaction from the second stage reaction mixture is removed by continuously circulating a portion of that mixture through a heat exchanger and thence back to the second reaction chamber.

Alternatively, the first and the second reaction chambers are both heat exchangers that provide a residence time in the range of 1 to about 10 minutes and that provide sufficient heat exchange surface in contact with the reaction mixture therein to enable removal of the heat of reaction generated within such residence time.

Effluent from the second reaction chamber is withdrawn at a rate sufficient to maintain a substantially constant volume of reaction mixture in the second reaction chamber, and preferably, the effluent from the first reaction chamber is withdrawn therefrom and fed to the second reaction chamber at a rate that maintains a substantially constant volume of reaction mixture in the first reaction chamber.

Preferably, the effluent from the second reaction chamber is caused/allowed to separate into (A) an inorganic phase comprising predominately ammonia, ammonium chloride and co-product thiophosphoric triamide, and (B) an organic phase comprising predominately N-hydrocarbylthiophosphoric triamide, tertiary amine, solvent and dissolved ammonia, and the resultant phases are separated from each other. This is preferably accomplished by allowing the effluent to stand in a quiescent state for a suitable period of time for the distinct separate phases to form and then draining off the lower layer. Other separation techniques such as siphoning off the top layer, use of emulsion breakers, and like procedures can be used whenever deemed necessary or desirable. After effecting this separation, it is preferred to separate ammonia along with a portion of the solvent from the isolated organic phase, and compress and cool this ammonia-solvent mixture to form a recycle mixture of liquid ammonia and solvent. This separation also provides as the residual mixture, a concentrated product mixture comprising predominately N-hydrocarbylthiophosphoric triamide, and residual solvent and tertiary amine. The recycle mixture of ammonia and the solvent remaining therewith is recycled for use as a portion of the ammonia feed to the second reaction chamber.

The concentrated product mixture is then processed so as to separate and recover tertiary amine and solvent therefrom, and the tertiary amine and solvent collected therewith are recycled for use as a portion of the feed for making the preformed mixture to be fed to the first reaction chamber. The residual portion of the organic phase remaining after this separation comprises N-hydrocarbylthiophosphoric triamide, and only small residual amounts of solvent and tertiary amine. Thereupon the N-hydrocarbylthiophosphoric triamide and the small residual amounts of solvent and tertiary amine are separated from each other to yield a purified N-hydrocarbylthiophosphoric triamide product. Either or both of this separated residual solvent and tertiary amine is/are recycled for use as a portion of the feed for making the preformed mixture fed to the first reaction chamber.

The specific techniques used for effecting the foregoing separations will depend to some extent upon the identities of the materials making up the mixtures being processed. Usually distillations or flash distillations will be employed whenever this is feasible. However, in any case where such distillation procedures are not feasible because of the properties of the materials being processed, recourse may be had to other separation techniques such as solvent extraction procedures, chromatographic separation procedures, or the like.

Reference will now be made to the continuous process depicted in FIGS. 1 and 2.

First Stage Reaction

In the embodiment depicted in FIGS. 1 and 2, triethylamine (TEA) and tetrahydrofuran (THF) are fed to the first reactor 10 as a mixture from a recycle solvent tank 12. Make-up THF and TEA stored in tanks 14 and 16, respectively, are added to recycle tank 12 as needed to maintain a constant solvent composition going to reactor 10. The feed rate is determined by maintaining a constant feed ratio of TEA to $PSCl_3$, based on periodic analyses of TEA in the TEA/THF mixture. This analysis should have +/−400 ppm (or better) resolution to allow control of the TEA/$PSCl_3$ mole ratio within 1–2% of target (1.10+/−0.02). TEA is consumed in this first reaction step and regenerated in the second reaction, while THF acts only as a solvent.

In first reactor 10, $PSCl_3$ (mass flow controlled) is reacted with n-butylamine (NBA) to form N-n-butylaminothiophosphoryl dichloride (BATPD) intermediate. The NBA is stored in tank 20 under nitrogen. Two different streams are fed to the reactor: 1) neat $PSCl_3$ from tank 18; and 2) mixed feeds of recycle THF/TEA and NBA from static mixer 22. The NBA feed rate is proportioned to the $PSCl_3$ feed rate to maintain a mole ratio of approximately 1.01 moles of NBA per mole of $PSCl_3$ and the THF/TEA feed rate is proportioned to the $PSCl_3$ feed rate to maintain a mole ratio of approximately 1.10 moles of TEA per mole $PSCl_3$.

Mixing is considered highly important for achieving very high efficiency in this reaction, and thus the NBA and THF/TEA are combined in static mixer 22 upstream of the reactor, and introduced to the reactor through a dip leg just above the agitator. The $PSCl_3$ is fed neat through a separate dip leg into the same area of the reactor. The HCl formed as co-product reacts with the TEA to form a TEA·HCl salt which precipitates from the reaction mass.

The reaction to form this intermediate BATPD is very exothermic, and most of this heat of reaction is removed by refluxing the THF solvent in a dephlegmator 24. Recommended reaction conditions in reactor 10 are 0–15° C. and, to allow solvent reflux, about 40–70 mm Hg (0.8–1.4 psia) pressure. Feed rates are adjusted to provide a three hour residence time in reactor 10. Since this reaction is very fast (1–2 minutes maximum) and irreversible, holdup in this reactor simply provides surge capacity for the process. Additional cooling for the reaction is provided by the reactor jacket and a pump-around loop through heat exchanger 26. The reaction mass discharge is fed continuously to the second reactor 30 via level control on first reactor 10.

Second Stage Reaction

In the second reactor 30, the intermediate BATPD from reactor 10 reacts with ammonia to give the final product, N-(n-butyl)thiophosphoric triamide (BTPT). The HCl generated by the reaction also reacts with ammonia to form ammonium chloride, and the TEA·HCl also reacts with ammonia to liberate the TEA and form additional ammonium chloride. A total of 5 moles of ammonia per mole BATPD is consumed in this step. This reaction is very exothermic, and the heat of reaction is removed via a pump-around loop through heat exchanger 32. Reaction conditions for reactor 30 are 8–15° C. and 25–38 psig, and the residence time is about 90 minutes.

Ammonia is fed by pressure control to reactor 30, and the ammonia feed consists of the recycle stream from product phase column 33 and fresh ammonia from storage vessel 34. A total of about 23–25 moles of ammonia per mole of BATPD is fed to reactor 30. Of this, about 14 moles is fresh ammonia. In order to keep the ammonium chloride co-product in solution, this amount of excess ammonia is used so that the ammonium chloride and the ammonia form a separate liquid phase containing about three moles of ammonia per mole of ammonium chloride. At lower ammonia levels, the ammonium chloride precipitates from the solution, forming a slurry which tends to cause pluggage problems. If the temperature in reactor 30 is allowed to go below about 6° C., the ammonium chloride/ammonia complex ($NH_4Cl \cdot 3NH_3$) will precipitate, which can also cause pluggage problems. Effluent discharge from this reactor is controlled to maintain constant level in reactor 30, and is sent to phase separator 36.

Phase Separation

The reaction mass coming from reactor 30 separates into two phases in phase separator 36, namely, (A) an inorganic phase containing ammonia, ammonium chloride, most of the by-product thiophosphoric triamide (TPT), and small amounts (<1%) of BTPT, THF and TEA; and (B) an organic phase containing THF, TEA, BTPT, some of the TPT, the other phosphorus by-product impurities, and ammonia. These are separated by gravity in separator 36 by employing a residence time therein of approximately 45 minutes. The separated phases are then stored, respectively, in two vessels, vessel 38 for the organic phase mixture and vessel 40 for the inorganic phase mixture. All three of these vessels (separator 36, and vessels 38 and 40) are maintained at the same pressure (40–50 psig) to allow gravity flow, and are cooled to hold a constant temperature (and thus constant composition and pressure). In the preferred system depicted, make-up ammonia can be fed directly to any of these drums from storage vessel 34, if the ammonia concentration becomes low enough to cause ammonium chloride precipitation.

As described in commonly-owned copending U.S. application Ser. No. 08/785,104, filed Jan. 21, 1997, all disclosure of which is incorporated herein by reference, the temperature of the mixture in which the triamide and ammonium chloride are being co-produced in a suitable organic solvent by reaction between N-hydrocarbylaminothiophosphoryl dichloride and a suitable amount of initially added and/or incrementally added ammonia (i.e., at least 16 and preferably at least 20 moles of ammonia per mole of ammonium chloride being formed) should be maintained above about 6° C. but below the temperature at which the triamide undergoes significant thermal degradation. A separate liquid phase containing the ammonium chloride (and ammonia) is formed, and can be readily separated, for example by a gravity separation, decantation procedures, or the like. At temperatures of about 6° C. and below, an ammonia-ammonium chloride complex forms as a solid phase which can cause pluggage of reaction equipment and which in any event detracts from the efficiency of the overall operation. Thus such low temperatures should be avoided. However, if in any special case where chemical or other considerations require or involve running the reaction at ≤6° C., the procedure can be modified to conduct the reaction at the lower temperature where the solid ammonia/ammonium chloride complex forms, and heating the final reaction mass above 6° C. to melt the complex thus forming the separate liquid ammoniate phase to allow phase separation and removal. The thermal degradation temperatures of the triamides usually differs at least to some extent from compound to compound, and thus the maximum permissible temperature may vary from compound to compound. In general, however, significant thermal degradation of the triamides is not incurred at temperatures of up to about 50° C. and in some cases perhaps not until up to still higher temperatures.

Organic Phase Distillation

The organic phase from vessel 38 is first distilled in product phase column 33 to remove dissolved ammonia and most of the solvents, i.e., THF and TEA. The ammonia stream (which contains about 25% THF) is recycled directly to the second stage reaction in reactor 30; the combined THF and TEA solvents are taken as a vapor side-stream from the column sump, condensed in condenser 35, and transferred via pump 37 to recycle solvent tank 12. The concentrated (bottoms) product solution (containing about 50% THF) is transferred to feed drum 42.

Column 33 is operated at about 7–8 psia pressure and 55° C. bottoms temperature to minimize thermal decomposition of the product. Built into the upper portion of column 33 is column dephlegmator condenser 46 which is used to cool the vapor and condense most of the THF as internal reflux. Two 2-stage blowers, 48 and 50 compress the ammonia vapor sufficiently (about 35 psig) to allow condensation and cooling with refrigerated Dowtherm® J coolant. This liquid ammonia/THF stream is then routed directly back to reactor 30.

Inorganic Phase Dilution

Typically, the inorganic phase (chiefly composed of ammonia and ammonium chloride) is first diluted with water and stored in storage tank 56, analyzed, and batch transferred to a railcar 58 prior to shipment. Preferably, the water added is proportioned to yield a co-product solution containing about 25% water, about 38% dissolved ammonium chloride and about 37% ammonia, which is a useful industrial product mixture. In order to suit specific industrial uses for the ammonia and ammonium chloride co-products, the amount of water added can be varied, and in fact, the addition of water can be entirely eliminated if desired.

As described in commonly-owned copending U.S. application Ser. No. 08/786,536, filed Jan. 21, 1997, all disclosure of which is incorporated herein by reference, it is desirable to inhibit the above aqueous solution of ammonia and ammonium chloride against ferrous metal corrosion by dissolving therein a ferrous metal corrosion-inhibiting amount of at least one water-soluble salt or oxide of zinc, aluminum, arsenic, antimony or bismuth, such as $Bi_2O_3$, ZnO, $ZnCl_2$, $AlCl_3$, and $Al_2O_3$. It is believed that corrosion by the uninhibited solutions is due to the presence of trace amounts of one or more impurities remaining in the solution, which impurities are probably, but not necessarily, one or more sulfur-containing impurities. Amounts of 1000 ppm (wt/wt) of such inhibitors have proven very effective, but any corrosion-inhibiting amount consistent with end-product usage and specifications can be employed.

Wiped-film Evaporation, Nitrogen Strip and Optional Dilution

The concentrated BTPT/THF/TEA solution from feed drum 42 is fed (by flow control) to wiped-film evaporator 44, to remove most of the remaining THF and TEA solvents. Wiped-film evaporator 44 is operated at about 110 mm Hg absolute and 95° C., producing a bottoms product containing <2% residual solvents. The solvent vapors from wiped-film evaporator 44 are condensed in heat exchanger 62, and the condensed solvent is recycled to recycle solvent tank 12 via pump 64. The bottoms product (predominately BTPT) from wiped-film evaporator 44 is fed (by level control on the bottoms receiver pot and pump 66) directly to the upper portion of nitrogen stripping column 68, in which hot nitrogen (about 65° C., atmospheric pressure) is passed upwardly in countercurrent flow to the down-flow product stream to further reduce the small residual solvent content of the BTPT to about 0.5% maximum. This neat product stream is then gravity fed into storage vessel 70 in which, if desired, it can be mixed with one or more solvents for storage and ultimate shipment.

We claim:

1. A process for separating or recovering N-hydrocarbylthiophosphoric triamide or N-hydrocarbylphosphoric triamide from a liquid mixture comprising N-hydrocarbylthiophosphoric triamide or N-hydrocarbylphosphoric triamide, inert organic solvent, and optionally tertiary amine, in which the process comprises continuously introducing a stream of such liquid mixture into a wiped film evaporator operating at a temperature in the range of about 60 to about 140° C., and at a pressure that avoids solids formation on the heating surface of the wiped film evaporator, and continuously collecting purified N-hydrocarbylthiophosphoric triamide or N-hydrocarbylphosphoric triamide so formed.

2. A process according to claim 1 wherein the inert organic solvent is a substance that boils at one or more temperatures in the range of about 40 to about 120° C. at ordinary atmospheric pressures, wherein tertiary amine is present, and wherein the tertiary amine is a substance that boils at one or more temperatures in the range of about 40 to about 130° C. at ordinary atmospheric pressures.

3. A process according to claim 1 wherein the inert organic solvent is a substance that boils at one or more temperatures in the range of about 55 to about 90° C. at ordinary atmospheric pressures, wherein tertiary amine is present, and wherein the tertiary amine is a substance that boils at one or more temperatures in the range of about 50 to about 100° C. at ordinary atmospheric pressures.

4. A process according to claim 1 wherein the average residence time of the triamide in the wiped-film evaporator is kept substantially constant throughout the operation, and is kept below about one minute.

5. A process according to claim 1 wherein the liquid mixture contains about 5 to about 60 wt. % of N-hydrocarbylthiophosphoric triamide or N-hydrocarbylphosphoric triamide, about 40 to about 95 wt. % of tetrahydrofuran, about 0 to about 20 wt. % triethylamine, and optionally, up to about 12 wt. % of one or more phosphorus-containing impurities.

6. A process according to claim 1 wherein the wiped film evaporator is operated at a temperature in the range of about 90 to about 130° C.

7. A process according to claim 1 wherein said triamide is N-alkylthiophosphoric triamide or N-alkylphosphoric triamide.

8. A process according to claim 1 wherein the inert solvent is tetrahydrofuran, wherein the tertiary amine is present, and wherein the tertiary amine is triethylamine.

9. A process according to claim 5 wherein the average residence time of the triamide in the wiped-film evaporator is kept substantially constant throughout the operation, and is kept below about one minute.

10. A process according to claim 9 wherein the wiped film evaporator is operated at a temperature in the range of about 90 to about 130° C.

11. A process according to claim 6 wherein the average residence time of the triamide in the wiped-film evaporator is kept substantially constant throughout the operation, and is kept below about one minute.

12. A process according to claim 1 wherein said triamide exists as a solid at room temperature and wherein the hydrocarbyl group of said triamide contains up to about 8 carbon atoms.

13. A process according to claim 12 wherein the hydrocarbyl group of said triamide is an alkyl group.

14. A process according to claim 13 wherein the wiped film evaporator is operated at a temperature in the range of about 90 to about 130° C., and wherein the average residence time of the triamide in the wiped-film evaporator is kept substantially constant throughout the operation, and is kept below about one minute.

15. A process according to claim 14 wherein the inert solvent is tetrahydrofuran, wherein the tertiary amine is present, and wherein the tertiary amine is triethylamine.

16. A process according to claim 15 wherein said triamide is an N-alkylthiophosphoric triamide.

17. A process according to claim 16 wherein said triamide is an N-n-butylthiophosphoric triamide.

18. A process for separating or recovering N-hydrocarbylthiophosphoric triamide from a liquid mixture comprising N-hydrocarbylthiophosphoric triamide, inert organic solvent, and optionally tertiary amine, said triamide being a substance that exists as a solid at room temperature, that melts in the range of 50 to 130° C. and that is soluble to the extent of at least 0.4 grams per milliliter at 20° C. in said solvent, said process comprising continuously introducing a stream of such liquid mixture into a wiped film evaporator operating at a temperature in the range of about 60 to about 140° C., and at a pressure that avoids solids formation on the heating surface of the wiped film evaporator, and continuously collecting purified N-hydrocarbylthiophosphoric triamide so formed.

19. A process according to claim 18 wherein the inert organic solvent is a substance that boils at one or more temperatures in the range of about 40 to about 120° C. at ordinary atmospheric pressures, wherein tertiary amine is present, and wherein the tertiary amine is a substance that boils at one or more temperatures in the range of about 40 to about 130° C. at ordinary atmospheric pressures.

20. A process according to claim 18 wherein the inert organic solvent is a substance that boils at one or more temperatures in the range of about 55 to about 90° C. at ordinary atmospheric pressures, wherein tertiary amine is present, and wherein the tertiary amine is a substance that boils at one or more temperatures in the range of about 50 to about 100° C. at ordinary atmospheric pressures.

21. A process according to claim 18 wherein the average residence time of the triamide in the wiped-film evaporator is kept substantially constant throughout the operation, and is kept below about one minute.

22. A process according to claim 18 wherein the liquid mixture contains about 5 to about 60 wt. % of N-hydrocarbylthiophosphoric triamide or N-hydrocarbylphosphoric triamide, about 40 to about 95 wt. % of tetrahydrofuran, about 0 to about 20 wt. % triethylamine, and optionally, up to about 12 wt. % of one or more phosphorus-containing impurities.

23. A process according to claim 18 wherein the wiped film evaporator is operated at a temperature in the range of about 90 to about 130° C.

24. A process according to claim 18 wherein said triamide is N-alkylthiophosphoric triamide or N-alkylphosphoric triamide.

25. A process according to claim 18 wherein the inert solvent is tetrahydrofuran, wherein the tertiary amine is present, and wherein the tertiary amine is triethylamine.

26. A process according to claim 22 wherein the average residence time of the triamide in the wiped-film evaporator is kept substantially constant throughout the operation, and is kept below about one minute.

27. A process according to claim 26 wherein the wiped film evaporator is operated at a temperature in the range of about 90 to about 130° C.

28. A process according to claim 23 wherein the average residence time of the triamide in the wiped-film evaporator is kept substantially constant throughout the operation, and is kept below about one minute.

29. A process according to claim 18 wherein said triamide exists as a solid at room temperature and wherein the hydrocarbyl group of said triamide contains up to about 8 carbon atoms.

30. A process according to claim 29 wherein the hydrocarbyl group of said triamide is an alkyl group.

31. A process according to claim 30 wherein the wiped film evaporator is operated at a temperature in the range of about 90 to about 130° C., and wherein the average residence time of the triamide in the wiped-film evaporator is kept substantially constant throughout the operation, and is kept below about one minute.

32. A process according to claim 31 wherein the inert solvent is tetrahydrofuran, wherein the tertiary amine is present, and wherein the tertiary amine is triethylamine.

33. A process for separating or recovering N-hydrocarbylthiophosphoric triamide or N-hydrocarbylphosphoric triamide from a liquid mixture comprising about 5 to about 60 wt. % of N-hydrocarbylthiophosphoric triamide or N-hydrocarbylphosphoric triamide, about 40 to about 95 wt. % of inert organic solvent, about 0 to about 20 wt. % of tertiary amine, and phosphorus-containing impurities in an amount corresponding to up to about 12 wt. % of phosphorus, said impurities being selected from thiophosphoric triamide, N,N'-dihydrocarbylthiophosphoric triamide, N,N',N"-trihydrocarbylthiophosphoric triamide, linear or cyclic oligomers of the hydrocarbylthiophosphoric triamide, phosphoric triamide, N, N'-dihydrocarbylphosphoric triamide, and linear or cyclic oligomers of the hydrocarbylphosphoric triamide, in which the process comprises continuously introducing a stream of such liquid mixture into a wiped film evaporator operating at a temperature in the range of about 60 to about 140° C., and at a pressure that avoids solids formation on the heating surface of the wiped film evaporator, and continuously collecting purified N-hydrocarbylthiophosphoric triamide or N-hydrocarbylphosphoric triamide so formed.

34. A process according to claim 33 wherein the wiped film evaporator is operated at a temperature in the range of about 90 to about 130° C.

35. A process according to claim 33 wherein the inert organic solvent is a substance that boils at one or more temperatures in the range of about 40 to about 120° C. at ordinary atmospheric pressures, wherein the tertiary amine is present, and wherein the tertiary amine is a substance that boils at one or more temperatures in the range of about 40 to about 130° C. at ordinary atmospheric pressures.

36. A process according to claim 33 wherein the inert organic solvent is a substance that boils at one or more temperatures in the range of about 55 to about 90° C. at ordinary atmospheric pressures, wherein the tertiary amine is present, and wherein the tertiary amine is a substance that boils at one or more temperatures in the range of about 50 to about 100° C. at ordinary atmospheric pressures.

37. A process according to claim 33 wherein the average residence time of the N-hydrocarbylthiophosphoric triamide or N-hydrocarbylphosphoric triamide in the wiped-film evaporator is kept substantially constant throughout the operation, and is kept below about one minute.

38. A process according to claim 33 wherein said N-hydrocarbylthiophosphoric triamide or N-hydrocarbylphosphoric triamide is N-alkylthiophosphoric triamide in which the alkyl group has 2 to 6 carbon atoms.

39. A process according to claim 33 wherein said N-hydrocarbylthiophosphoric triamide or N-hydrocarbylphosphoric triamide is N-n-butylthiophosphoric triamide.

40. A process according to claim 39 wherein the inert solvent is tetrahydrofuran, wherein the tertiary amine is present, and wherein the tertiary amine is triethylamine.

41. A process according to claim 33 wherein the wiped film evaporator is operated at a temperature in the range of about 90 to about 130° C.; wherein the inert organic solvent is a substance that boils at one or more temperatures in the range of about 40 to about 120° C. at ordinary atmospheric pressures; wherein the tertiary amine is present; wherein the tertiary amine is a substance that boils at one or more temperatures in the range of about 40 to about 130° C. at ordinary atmospheric pressures, wherein the average residence time of the N-hydrocarbylthiophosphoric triamide or N-hydrocarbylphosphoric triamide in the wiped-film evaporator is kept substantially constant throughout the operation, and is kept below about one minute.

42. A process according to claim 41 wherein said N-hydrocarbylthiophosphoric triamide or N-hydrocarbylphosphoric triamide is N-alkylthiophosphoric triamide in which the alkyl group has 2 to 6 carbon atoms.

43. A process according to claim 41 wherein said N-hydrocarbylthiophosphoric triamide or N-hydrocarbylphosphoric triamide is N-n-butylthiophosphoric triamide.

44. A process according to claim 43 wherein the inert solvent is tetrahydrofuran, and wherein the tertiary amine is triethylamine.

* * * * *